(12) United States Patent
Cao et al.

(10) Patent No.: US 11,004,564 B2
(45) Date of Patent: May 11, 2021

(54) METHOD AND APPARATUS FOR PROCESSING MEDICAL DATA

(71) Applicant: International Business Machines Corporation, Armonk, NY (US)

(72) Inventors: Feng Cao, ShangHai (CN); Xiang Li, Beijing (CN); Jing Mei, Beijing (CN); Yuan Ni, ShangHai (CN); Weijia Shen, Beijing (CN); Wen Sun, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 321 days.

(21) Appl. No.: 16/053,086

(22) Filed: Aug. 2, 2018

(65) Prior Publication Data

US 2018/0366226 A1    Dec. 20, 2018

Related U.S. Application Data

(63) Continuation of application No. 14/186,079, filed on Feb. 21, 2014, now Pat. No. 10,068,668.

(30) Foreign Application Priority Data

Feb. 28, 2013   (CN) .......................... 201310064224.4

(51) Int. Cl.
*G16H 50/20* (2018.01)
*G16H 10/60* (2018.01)
*G06F 19/00* (2018.01)

(52) U.S. Cl.
CPC ............. *G16H 50/20* (2018.01); *G06F 19/00* (2013.01); *G16H 10/60* (2018.01)

(58) Field of Classification Search
None
See application file for complete search history.

(56) References Cited

U.S. PATENT DOCUMENTS 6,272,480 B1    8/2001 Tresp et al.
2004/0083084 A1 4/2004 West
(Continued)

FOREIGN PATENT DOCUMENTS

CN          1588308 A      3/2005
CN        101388006 A      3/2009
(Continued)

OTHER PUBLICATIONS

Office Action in U.S. Appl. No. 14/186,079 dated May 9, 2016.
(Continued)

*Primary Examiner* — Eliza A Lam
(74) *Attorney, Agent, or Firm* — Kristofer Haggerty, Esq.; McGinn I.P. Law Group, PLLC.

(57) ABSTRACT

A computer implemented method for processing a plurality of medical indication conditions on a computer that includes a processor communicatively coupled to a memory includes obtaining a plurality of predetermined indication conditions which relate to a plurality of parameters, and forming a plurality of conditional segments based on respective values of the plurality of parameters defined in the plurality of predetermined indication conditions. Each conditional segment of the plurality of conditional segments corresponds to a combination of different value ranges of respective parameters of the plurality of parameters. The plurality of predetermined indication conditions includes a measurement item, a reference standard, a time period, a measurement condition, and a measurement manner.

20 Claims, 5 Drawing Sheets

(56) References Cited

U.S. PATENT DOCUMENTS

| | | | |
|---|---|---|---|
| 2007/0112782 A1 | 5/2007 | Labach et al. | |
| 2007/0112827 A1* | 5/2007 | Dettinger | G06F 16/2465 |
| 2007/0118399 A1 | 5/2007 | Avinash et al. | |
| 2008/0133275 A1* | 6/2008 | Haug | G06Q 50/24 |
| | | | 705/3 |
| 2009/0192822 A1 | 7/2009 | Regulapati et al. | |
| 2010/0138231 A1 | 6/2010 | Linthicum et al. | |
| 2011/0201902 A1* | 8/2011 | Shiga | G06F 19/00 |
| | | | 600/300 |
| 2012/0203089 A1 | 8/2012 | Rule et al. | |

FOREIGN PATENT DOCUMENTS

| | | |
|---|---|---|
| CN | 101938939 A | 1/2011 |
| CN | 101990673 A | 3/2011 |
| WO | WO-2008/079341 | 7/2008 |

OTHER PUBLICATIONS

Office Action in U.S. Appl. No. 14/186,079 dated Nov. 9, 2016.
Office Action in U.S. Appl. No. 14/186,079 dated Aug. 9, 2017.
Office Action in U.S. Appl. No. 14/186,079 dated Feb. 5, 2018.
"Bayes' Theorem Illustrated (My Way)" "http://lesswrong.com/lw/2b0/bayes_theorem_illustrated_my_way/" Published Jun. 3, 2010 Accessed Feb. 3, 2018.
Notice of Allowance in U.S. Appl. No. 14/186,079 dated May 3, 2018.
Notice of Allowance in U.S. Appl. No. 14/186,079 dated Jul. 18, 2018.
Sordo et al., Gello: An object-oriented query and expression language for clinical decision support, AMIA 2003 Open Source Expo.
Mark Ebell, AHRQ White Paper: Use of clinical decision rules for point-of-care decision support, Sage Journals, Nov./Dec. 2010.
Robert A. Greenes, Features of computer-based clinical decision support, Clinical Decision Support: The Road Ahead, 2007, 79-107, Academic Press.
Infrastructure for on demand evidence adaptive clinical decision support system (OCDSSI), The IP.com Prior Art Database Disclosure IPCOM000137109D, Jun. 8, 2006.
Chinese Office Action dated Aug. 2, 2016.
Chinese Office Action, dated Nov. 15, 2017, in Chinese Application No. 201310064224.4.
"Accounting Positive Research Methods" Dongbei University of Finance & Economics Press: PN 130369, 2012.
English translation of Chinese Office Action dated Oct. 8, 2018 in Chinese Patent Application No. 2013-10064224.4.

* cited by examiner

METHOD AND APPARATUS FOR PROCESSING MEDICAL DATA

CROSS-REFERENCE TO RELATED APPLICATION

The present application is a Continuation Application of U.S. patent application Ser. No. 14/186,079, filed on Feb. 21, 2014, which is based on Chinese Patent Application No. 201310064224.4 filed on Feb. 28, 2013, the contents of which is incorporated herein by reference in its entirety.

BACKGROUND OF THE INVENTION

The present invention relates to the field of data processing. More specifically, the present invention relates to a method and an apparatus for processing data in the medical field.

With the widespread move to medical electronization, Electronic Health Records (EHR) are used to record the relevant medical data of patients. Usually, an EHR includes basic information, main diseases, and all the clinical records of a patient. The clinical record records clinical conditions of a patient at different times (i.e., each time a patient visits a doctor, every day during a given time period, etc.), which includes diagnosis, examination, and lab test results (such as measurement results concerning various physiological states). The existing EHR typically uses the XML language to record patient data in the form of a Clinical Document Architecture (CDA).

On the other hand, authorities have issued clinical guidelines directed to different diseases with a lot of clinical practice and clinical evidence to help a doctor to fully understand the conditions of a patient. Generally, a clinical guideline includes a plurality of indications as well as judgment conditions of the indications. For instance, a clinical guideline concerning diabetes can contain an indication 1 of a controlled blood glucose and an indication 2 of a persistently high blood glucose. The condition of the indication 1 is that 80% of blood glucose value in the latest one month satisfies fasting blood glucose<7.5 mmol/L or 2 h blood glucose<10 mmol/L. The condition of the indication 2 is that 80% of blood glucose value in latest three months satisfies fasting blood glucose>=9 mmol/L or 2 h blood glucose>=13 mmol/L. Determination of a single indication cannot be directly used for performing diagnosis and treatment of a disease, but a combination of a plurality of indications can help a doctor to fully acquire comprehensive information of a patient. Since judgment and matching of indications can be based on measurement results of a patient, therefore, it is desired to acquire patient data from an EHR and process patient data to match it with indication conditions in a clinical guideline and to provide more comprehensive patient information.

FIG. 1 schematically shows the manner of processing patient data in the prior art. As shown in FIG. 1, when matching and analysis are required for a plurality of indication conditions 1-n in a clinical guideline, a data acquisition step 101, a data conversion step 102, and a condition matching step 103 are executed one by one as to each indication condition. Specifically, as to a certain indication condition i, at the data acquisition step 101, patient data required by the indication condition i is acquired. For instance, as to indication condition of the above indication 1, it is required to obtain fasting blood glucose data and 2 h blood glucose data of a patient in the latest one month. Then, at the data conversion step 102, the obtained data is converted into a certain needed form. As mentioned above, the existing EHR uses a XML language to record the patient data in form of CDA. However, this form is not convenient for direct data analysis and matching. Therefore, at step 102, patient data is converted from the CDA form to a form of Virtual Medical Record (VMR). The VMR form can be represented as a tree structure with the patient as a root node and respective attributes of observed results as leaf nodes. By going through the tree structure, at conditional matching step 103, the patient data can be matched with the indication condition i, which means to analyze whether the patient data meets the indication condition i. After matching the indication condition i, the next indication condition is analyzed according to the same steps 101-103. Thus, matching condition of the patient data with the respective indication conditions in the clinical guideline can be obtained by processing and analyzing the patient data.

However, the above manner of processing the patient data is not ideal in execution efficiency. The non-ideal efficiency is partly caused by redundant data processing. For instance, in order to analyze the indication condition 1, it is required to obtain fasting blood glucose data and 2 h blood glucose data of a patient in the latest one month. In order to analyze the indication condition 2, fasting blood glucose data and 2 h blood glucose data of the patient in the latest three months is obtained. Though data required by the indication condition 2 covers the data required by the indication condition 1, according to the method of FIG. 1, when the indication condition 2 is analyzed, it still requires retrieval again from an EHR of all the blood glucose data in the latest three months. As a result, the blood glucose data in the recent one month is retrieved repeatedly when analyzing the indication condition 1 and the indication condition 2. Further, at the data conversion step 102, the data above is converted again. At condition matching step 103, the above data is traversed for many times again. Obviously, such redundant processing reduces processing efficiency of the patient data. In practice, a clinical guideline for a certain disease usually contains more than one hundred, or even hundreds, of indication conditions. Since there are many indication conditions to be analyzed, processing of the patient data usually costs a lot of time and cannot be performed in real-time. This makes a doctor unable to obtain comprehensive information of a patient in efficient time.

Therefore, an improved solution is desired to improve processing efficiency of patient data.

SUMMARY OF THE INVENTION

In consideration of the above-mentioned problems existing in the prior art, the present invention improves processing efficiency of patient data.

Accordingly, a first aspect of the present invention provides a method for processing indication conditions, including: obtaining a plurality of predetermined indication conditions which relate to a plurality of parameters; and forming a plurality of conditional segments based on respective values of the plurality of parameters defined in the plurality of indication conditions, wherein the plurality of conditional segments respectively correspond to a plurality of combinations of value ranges of the plurality of parameters.

A second aspect of the present invention provides a method for processing patient data, including: obtaining distribution information of the patient data in a plurality of conditional segments formed as to a plurality of indication conditions using the method according to the first aspect; and determining a matching relation of the patient data with at least one indication condition of the plurality of indication conditions based on the distribution information.

A third aspect of the present invention provides an apparatus for processing indication conditions, including: an indication condition obtaining unit configured to obtain a plurality of predetermined indication conditions which relate to a plurality of parameters; and a conditional segment forming unit configured to form a plurality of conditional segments based on respective values of the plurality of parameters defined in the plurality of indication conditions, wherein the plurality of conditional segments respectively correspond to a plurality of combinations of value ranges of the plurality of parameters.

A fourth aspect of the present invention provides an apparatus for processing patient data, including: a distribution obtaining unit configured to obtain distribution information of the patient data in a plurality of conditional segments formed as to a plurality of indication conditions using the apparatus according to the third aspect; and a matching determining unit configured to determine a matching relation of the patient data with at least one indication condition of the plurality of indication conditions based on the distribution information.

Using the methods and apparatuses of the embodiments of the present invention, matching related patient data with a plurality of indication conditions can be directly determined based on distribution information of the patient data in the respective formed conditional segments. As the number of times redundant data is obtained and data conversion is reduced, the methods and apparatuses of the embodiments of the present invention improve processing efficiency of patient data.

BRIEF DESCRIPTION OF THE DRAWINGS

Through the more detailed description of some embodiments of the present invention in the accompanying drawings, the above and other objects, features, and advantages of the present invention are made more apparent. The same reference generally refers to the same components in the embodiments of the present invention.

FIG. 5A shows conditional segments of two levels;
and
FIG. 5B shows conditional segments of three levels.

DETAILED DESCRIPTION OF THE PREFERRED EMBODIMENT

Figure 1:
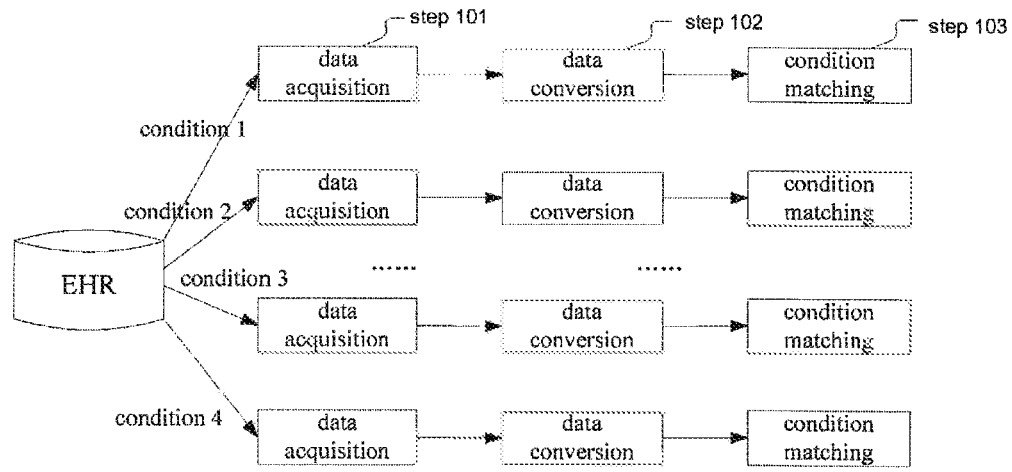
FIG. 1 schematically shows the manner of processing patient data in the prior art.

Some preferable embodiments are described in more detail with reference to the accompanying drawings, in which the preferable embodiments of the present invention have been illustrated. However, the present invention can be implemented in various manners and, thus, should not be construed to be limited to the embodiments disclosed herein. On the contrary, those embodiments are provided for the thorough and complete understanding of the present invention and to completely convey the scope of the present invention to those skilled in the art.

As can be appreciated by one skilled in the art, aspects of the present invention can be embodied as a system, method, or computer program product. Accordingly, aspects of the present invention can take the form of an entirely hardware embodiment, an entirely software embodiment (including firmware, resident software, micro-code, etc.), or an embodiment combining software and hardware aspects that can all generally be referred to herein as a "circuit," "module," or "system." Furthermore, aspects of the present invention can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium can include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain or store a program for use by or in connection with an instruction execution system, apparatus, or device.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be any computer readable medium that is not a computer readable storage medium and that can communicate, propagate, or transport a program for use by or in connection with an instruction execution system, apparatus, or device.

Program code embodied on a computer readable medium can be transmitted using any appropriate medium, including but not limited to wireless, wireline, optical fiber cable, RF, etc., or any suitable combination of the foregoing.

Computer program code for carrying out operations for aspects of the present invention can be written in any combination of one or more programming languages, including an object oriented programming language such as Java, Smalltalk, C++ or the like, and conventional procedural programming languages, such as the "C" programming language or similar programming languages. The program code can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

Aspects of the present invention are described below with reference to flowchart illustrations and/or block diagrams of methods, apparatus (systems), and computer program products according to embodiments of the invention. It can be understood that each block of the flowchart illustrations and/or block diagrams and combinations of blocks in the flowchart illustrations and/or block diagrams can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions can also be loaded onto a computer, other programmable data processing apparatus, or other devices to cause a series of operational steps to be performed on the computer, other programmable apparatus, or other devices to produce a computer implemented process such that the instructions which execute on the computer or other programmable apparatus provide processes for implementing the functions/acts specified in the flowchart and/or block diagram block or blocks.

Figure 2:
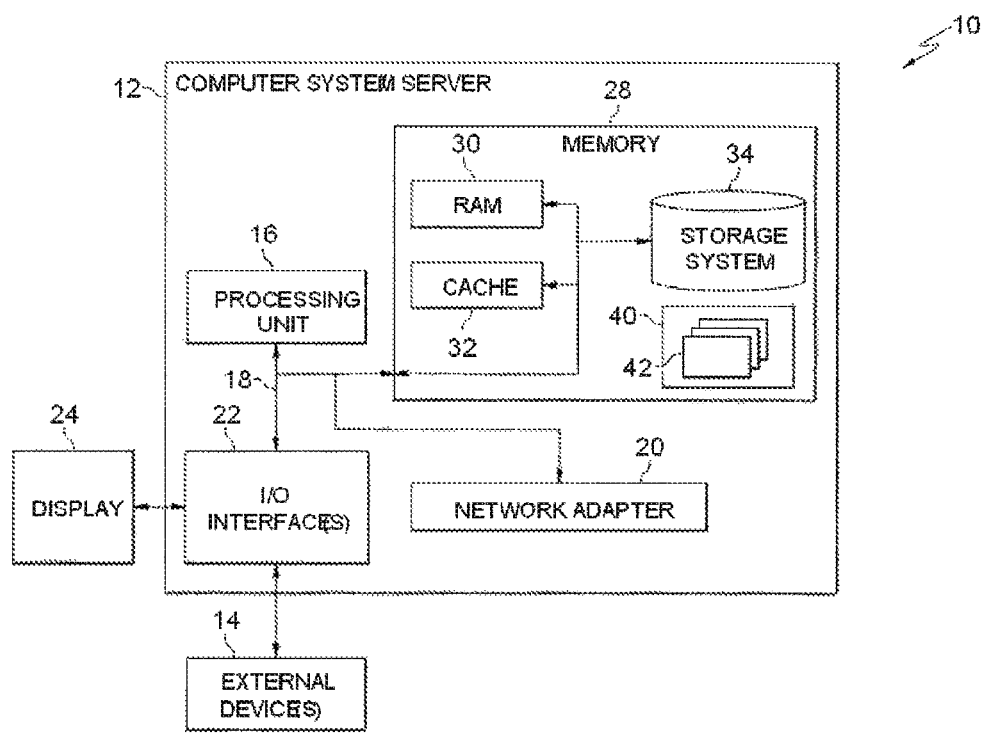
FIG. 2 shows a block diagram of an exemplary computer system/server which is applicable to implement the embodiments of the present invention.

Refer now to FIG. 2, in which an exemplary computer system/server 12 which is applicable to implement the embodiments of the present invention is shown. Computer system/server 12 is only illustrative and is not intended to suggest any limitation as to the scope of use or functionality of embodiments of the present invention described herein.

As shown in FIG. 2, computer system/server 12 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12 and it includes both volatile and non-volatile media and removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk") and an optical disk drive for reading from or writing to a removable, non-volatile optical disk such as a CD-ROM, DVD-ROM or other optical media can be provided. In such instances, each can be connected to bus 18 by one or more data media interfaces. As is further depicted and described below, memory 28 can include at least one program product having a set (e.g., at least one) of program modules that are configured to carry out the functions of embodiments of the present invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14, such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components can be used in conjunction with computer system/server 12. Examples, include, but are not limited to: microcode, device drivers, redundant processing units, external disk drive arrays, RAID systems, tape drives, and data archival storage systems, etc.

Below, executing manners of the present invention are described with reference to the Figures. According to embodiments of the present invention, in comprehensive consideration of a plurality of indication conditions, a plurality of conditional segments are formed based on respective parameters involved in the indication conditions. Then distribution of patient data in respective conditional segments is analyzed and a matching relation of the patient data with the respective indication conditions is determined based on such distribution information. Thus, redundant data obtaining and data converting operations are lessened or avoided. Respective embodiments of the present invention for implementing the idea above are described in detail below.

Figure 3:
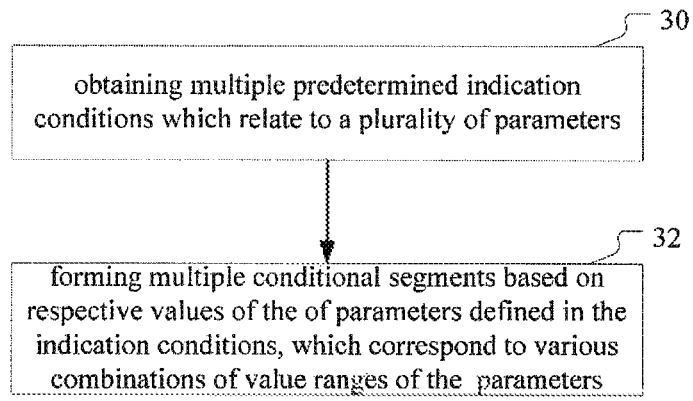
FIG. 3 shows a method for processing indication conditions according to an embodiment of the present invention.

Reference is now made to FIG. 3, which illustrates a method for processing indication conditions according to an embodiment of the present invention. As shown in FIG. 3, a method for processing medical indication conditions according to an embodiment of the present invention includes: step 30, obtaining a plurality of predetermined indication conditions which relate to a plurality of parameters; and step 32, forming a plurality of conditional segments based on respective values of the plurality of parameters defined in the plurality of indication conditions, wherein the plurality of conditional segments respectively correspond to a plurality of combinations of value ranges of the plurality of parameters. Below, executions of the respective steps above are described in combination with concrete examples.

First, at step 30, a plurality of predetermined indication conditions are obtained. In an embodiment of the present invention, the plurality of predetermined indication conditions are indication conditions contained in a clinical guideline. As the clinical guideline is already recorded and stored in computerized manner according to prior art, therefore, at step 30, several indication conditions of interest can be read directly from the computerized clinical guideline. In a concrete example, the plurality of indication conditions refer to all indication conditions contained in a clinical guideline directed to a certain disease. It can be appreciated, in other embodiments of the present invention, that predefined indication conditions can also be obtained from other data sources. Generally, an indication condition relates to a plurality of parameters which typically include measurement item, reference standard, and time period. In some cases, the indication conditions can further relate to other parameters, such as measurement conditions, measurement manners, etc.

Based on respective values of the plurality of parameters defined in the plurality of indication conditions mentioned above, at step 32, a plurality of conditional segments are formed, wherein the plurality of conditional segments respectively correspond to a plurality of combinations of different value ranges of the plurality of parameters. Below, execution of the step 32 above is described in connection with examples of three indication conditions.

Indication 1: Controlled Blood Glucose

Indication Condition 1: 80% of blood glucose values in the recent one month satisfies: fasting blood glucose<7.5 mmol/L or 2 h blood glucose<10 mmol/L.

Indication 2: Blood Glucose Continues High

Indication Condition 2: 80% of blood glucose values in the recent three months satisfies: fasting blood glucose>=9 mmol/L or 2 h blood glucose>=13 mmol/L.

Indication 3: Hypoglycemia

Indication Condition 3: the latest blood glucose<3.9 mmol/L.

As can be seen, all the parameters involved in the Indication Conditions 1-3 above include measurement item, reference standard, and time period. In Indication Condition 1, the measurement item is valued as fasting blood glucose or 2 h blood glucose, the reference standard is valued as fasting blood glucose 7.5 mmol/L as well as 2 h blood glucose 10 mmol/L, and the time period is valued as the most recent one month. Similarly, values of parameters (measurement item, reference standard, and time period) involved in Indication Conditions 2 and 3 can be obtained. Based on the values, at step 32, a plurality of conditional segments are formed to define a plurality of possible states of the patient data.

Figure 4:
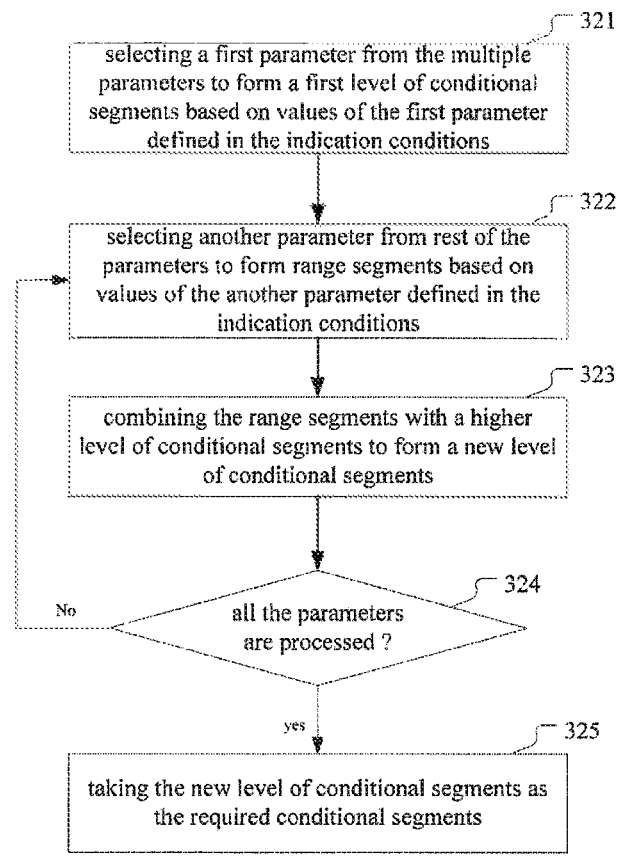
FIG. 4 shows sub-steps of a method for forming a plurality of conditional segments according to an embodiment of the present invention.

FIG. 4 shows sub-steps of forming a plurality of conditional segments according to an embodiment of the present invention (i.e. sub-steps of the step 32 above). As shown in FIG. 4, first, at step 321, a first parameter is selected from the plurality of parameters to form a first level of conditional segments based on values of the first parameter defined in the plurality of indication conditions. Then, at step 322, another parameter is selected from the rest of the parameters to form a plurality of range segments based on values of the other parameter defined in the plurality of indication conditions. At step 323, the plurality of range segments are combined with conditional segments in a higher level to form a new level of conditional segments. Then, at step 324, it is judged whether the plurality of parameters have been processed. If they have not, steps 322-324 can be executed repeatedly until all the plurality of parameters are processed. In case that all the plurality of parameters have been processed, at step 325, conditional segments of the newest level formed now is determined as the plurality of conditional segments required.

As to the Indication Conditions 1-3 above, involved parameters include measurement item, reference standard, and time period. In an example, at step 321, the measurement item is selected as a first parameter. Furthermore, values of the first parameter in respective indication conditions are obtained. As to the measurement item, values given by Indication Conditions 1-3 include fasting blood glucose and 2 h blood glucose, wherein the blood glucose measurement in Indication Condition 3 includes the fasting blood glucose and 2 h blood glucose. Therefore, a first level of conditional segments is formed based on the two values. In other words, at the first level, 2 conditional segments (i.e. fasting blood glucose and 2 h blood glucose) are defined so as to divide patient data into two parts which respectively meet the two conditional segments.

Then, at step 322, another parameter is selected from the rest of the parameters and values of the another parameter in respective indication conditions are obtained to form a plurality of range segments. As the measurement item has been selected as a first parameter, in an example, the reference standard is selected as another parameter. After analyzing the Indication Conditions 1-3, respective values of the reference standard can be easily extracted to obtain the following information: the Indication Condition 1 has the following defined values of the reference standard: 7.5 mmol/L and 10 mmol/L; values defined by the Indication Condition 2 include: 9 mmol/L and 13 mmol/L; and a value defined in the Indication Condition 3 includes 3.9 mmol/L. Based on such information, respective values obtained from the extraction are ordered and adjacent values are combined as a segment so as to obtain a plurality of value ranges. For respective values of the reference standard above, the following range segments can be formed: <3.9, [3.9, 7.5), [7.5, 9), [9, 10), [10, 13), and >=13.

Then, at step 323, the plurality of range segments are combined with conditional segments in a higher level to form a new level of conditional segments. In the current example, conditional segments in the higher level are the first level conditional segments formed at step 321. More specifically, two conditional segments defined by the fasting blood glucose and 2 h blood glucose. Thus, at step 323, the plurality of range segments formed by respective values of the reference standard are used to further divide the 2 conditional segments of the first level to form a new level of conditional segments. In an example, respective range segments formed are directly combined with respective conditional segments of a higher level. In this case, if there has formed "n" conditional segments in the higher level and "m" ranges at step 322, then n*m conditional segments are obtained in the new level. In another embodiment of the present invention, the association between parameters defined in respective indication conditions is taken into consideration to combine the range segments formed at step 322 with conditional segments of higher level. Specifically, the value "<7.5" of the reference standard defined in Indication Condition 1 is only directed to the fasting blood glucose and the value "<10 mmol/L" of the reference standard is only directed to the 2 h blood glucose. Therefore, the range segment which relates to the value 7.5 mmol/L is only required to be combined with the conditional segment of the fasting blood glucose in the first level and the range segment which relates to the value 10 mmol/L is only required to be combined with the conditional segment of the 2 h blood glucose in the first level.

Figure 5A:
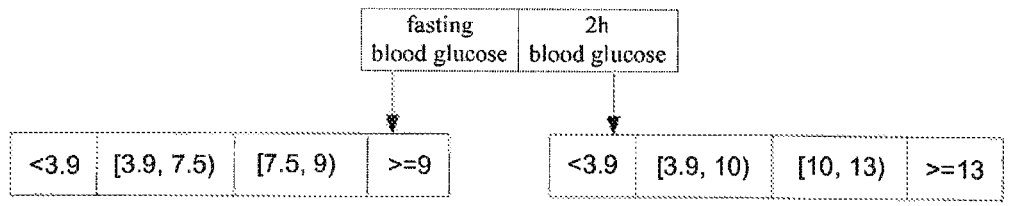
FIGS. 5A-5B show a process diagram of forming conditional segments according to an embodiment of the present invention. More specifically.

FIG. 5 shows a process diagram of forming conditional segments according to an embodiment of the present invention. In particular, FIG. 5A shows conditional segments of two levels, wherein the first level of conditional segments is formed based on values of measurement item at step 321 and the second level of conditional segments is formed based on values of the reference standard as mentioned before in steps 322 and 323. Specifically, in FIG. 5A, the association between the measurement item and reference standard defined in the indication conditions is considered and, therefore, in the second level only range segments <3.9, [3.9, 7.5), [7.5, 9), >=9 are combined with the conditional segment "fasting blood glucose" in the first level. Correspondingly, range segments in combination with the conditional segment "2 h blood glucose" in the first level are: <3.9, [3.9, 10), [10, 13), >=13. Therefore, at the second level, 8 conditional segments are formed.

As mentioned above, it is necessary to execute steps 322-323 repeatedly until all the plurality of parameters are processed. The conditional segments formed in FIG. 5A only take the two parameters of measurement item and reference standard into consideration. Therefore, then, as to the rest another parameter (i.e. time period) steps 322 and 323 are executed again.

Figure 5B:
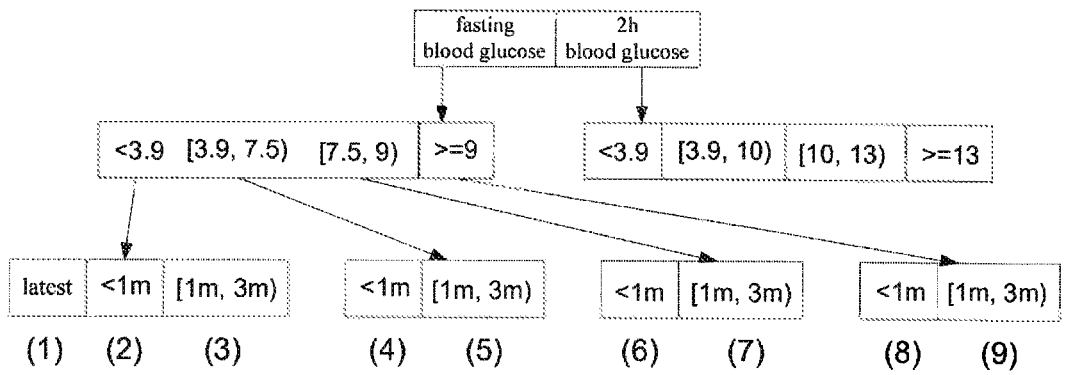

Similarly, at step 322, values of the other parameter "time period" in respective indication conditions are obtained to form a plurality of range segments. In Indication Conditions 1-3, the following values are defined as to the time period: the recent one month, the recent three months, and the latest time. Thus, the following range segments can be formed: the latest time, within the recent one month, and from the recent one month to three months. The range segments can be expressed as: latest, <1 m, [1 m, 3 m). Then, at step 323, the plurality of range segments above are combined with conditional segments in higher levels (i.e. conditional segments in the first and second levels as shown in FIG. 5A to form a new level of conditional segments). As mentioned above, by considering the association between the parameters defined in the indication conditions, it can be determined that the range segment of "the latest" is only specified in association with the reference standard <3.9 in the Indication Condition 3 and, thus, this range segment is only required to be combined with conditional segment of "<3.9" among the higher level conditional segments. Therefore, by combining the range segments formed by the time period with conditional segments of higher levels selectively, a third level of conditional segments is formed as shown in FIG. 5B. These conditional segments are number-labeled as conditional segments (1)-(9). In FIG. 5B, conditional segments of the branch of 2 h blood glucose in the third level is omitted for clarity and conciseness.

As to the Indication Conditions 1-3, by executing the steps 321-323 above, a plurality of conditional segments, as shown in FIG. 5B, are formed in levels. At this time, the parameters (i.e. measurement item, reference standard, and time period) involved in the Indication Conditions 1-3 have all been processed. Therefore, the formed new level conditional segments (i.e. the third level conditional segments) are taken as required conditional segments. Here, each conditional segment corresponds to a combination of different value ranges of respective parameters. For instance, the conditional segment (1) corresponds to a combination that the measurement item is valued as fasting blood glucose, the reference standard is valued as <3.9 mmol/L, and the time period is valued as "the latest" at the same time. The conditional segment (4) corresponds to a combination that the measurement item is valued as fasting blood glucose, the reference standard is valued as [3.9, 7.5), and the time period is valued as within one month.

Figure 6:
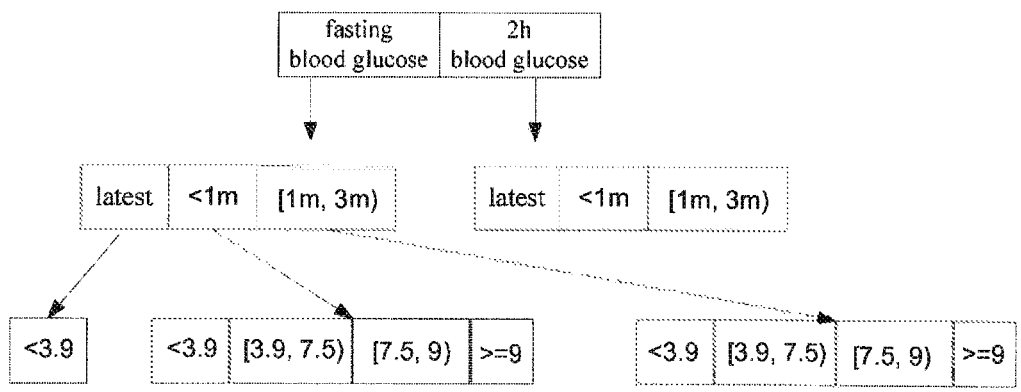
FIG. 6 shows a plurality of conditional segments formed according to an embodiment of the present invention.

In order to form the needed conditional segments, in the forming process as shown in FIG. 5, at the first level, measurement item is selected as a first parameter to form conditional segments of the first level based on the values thereof. Then, at the second and the third levels, new levels of conditional segments are formed based on values of the reference standard and time period, respectively. However, such selection order is not the only choice. In an example, at step 321, the first level conditional segments are formed still based on values of the measurement item. However, then, at the second level, conditional segments are formed based on values of the time period and then the third level conditional segments are formed based on value of the reference standard. Thus, conditional segments as shown in FIG. 6 are obtained.

Figure 7:
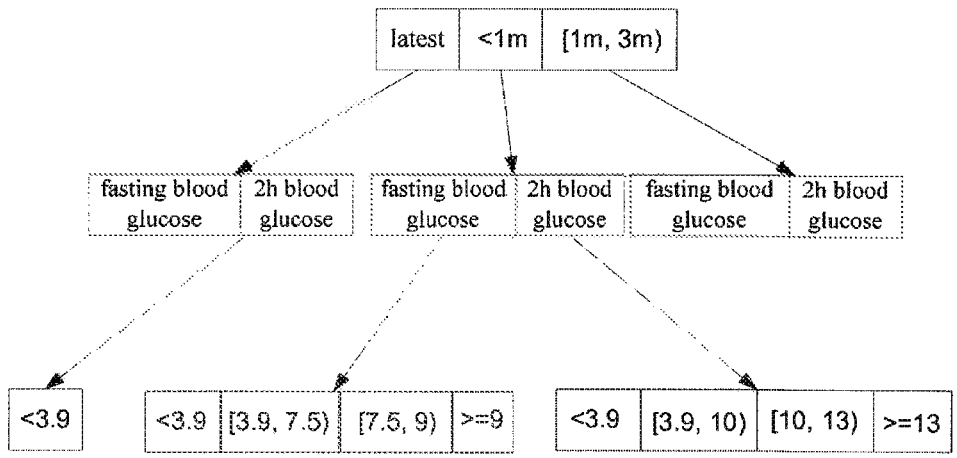
FIG. 7 shows a plurality of conditional segments formed according to another embodiment of the present invention.

In another example, at step 321, the first level conditional segments are formed based on values of the time period. Then, the second level conditional segments are formed based on the measurement item and the last level conditional segments are formed based on values of the reference standard. Accordingly, the conditional segments as shown in FIG. 7 are obtained. It can be appreciated that other orders are also possible to form the respective conditional segments.

Formation of conditional segments are described in connection with examples of concrete Indication Conditions 1-3 above. It can be appreciated, in other examples, that the parameters in the indication conditions can have different values than those in the examples above. For instance, the measurement item can further be valued as blood lipid, blood pressure, etc. Correspondingly, the reference standard can also be different. With respect to these different examples, steps 321-323 can be executed similarly to obtain required conditional segments. More generally, it is possible that other indication conditions can relate to different parameters or more parameters, such as measurement condition, measurement manner, etc. In these cases, besides executing steps 321-323 above for different parameters similarly, it can be necessary to execute steps 322-323 for more times repeatedly to process more parameters to obtain conditional segments of more levels.

The conditional segments formed in the method above respectively correspond to various combinations of value ranges of parameters defined in respective indication conditions. Such combinations can further be used for dividing patient data and, thus, matching the patient data with respective indication conditions. In other words, the conditional segments formed directed to the indication conditions can be used for processing patient data. More specifically, for analyzing the matching of the patient data with respective conditions.

Figure 8:
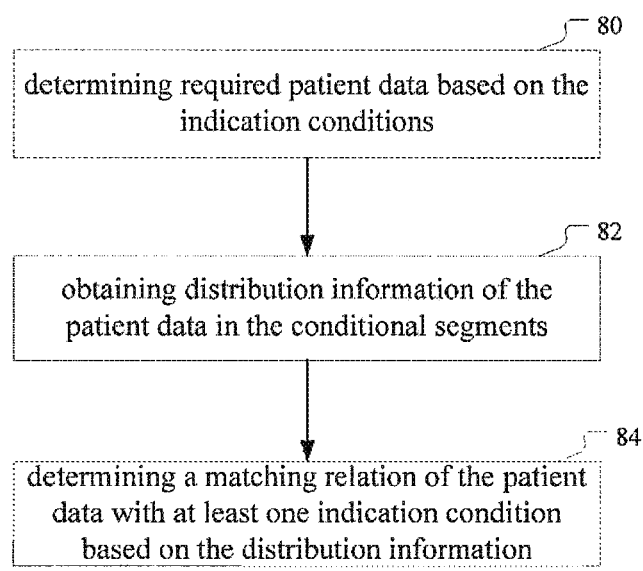
FIG. 8 shows a method for processing patient data according to an embodiment of the present invention.

Therefore, based on the conditional segments formed above, embodiments of the present invention further provide a method for processing patient data. FIG. 8 is a flowchart showing a method for processing patient data according to an embodiment of the present invention. As shown in FIG. 8, at step 82, distribution information of the patient data in a plurality of conditional segments formed directed to a plurality of indication conditions using the method above is obtained. At step 84, a matching relation of the patient data with at least one indication condition of the plurality of indication conditions is determined based on the distribution information. Below, concrete execution processes of the steps above are described.

At step 82, distribution information of patient data in a plurality of conditional segments is obtained and the plurality of conditional segments are formed according to the method in FIG. 3 directed to a plurality of indication conditions. In an embodiment of the present invention, counters are set for the respective formed conditional segments and, at step 82, numbers of patient data falling into corresponding conditional segments are counted using counters of respective conditional segments. Specifically, at step 82, patient data is obtained from an EHR and a format conversion is performed on the patient data when necessary. Based on this, respective patient data is matched with respective formed conditional segments. Specifically, attribute values of the patient data (such as measurement time, measurement item, and measurement values) are compared to value ranges of parameters corresponding to respective conditional segments so as to determine a conditional segment to which the patient data belongs. As to a specific conditional segment, once certain patient data is determined as belonging to said conditional segment or matching with the conditional segment, the counter of the specific conditional segment is incremented by 1. Thus, counters of respective conditional segments can reflect the number of patient data falling into the corresponding conditional segments. Therefore, statistical results of respective conditional segments can be obtained by reading the counting of the counters of respective conditional segments so as to obtain distribution of the patient data in respective conditional segments.

Specifically, as to some specific conditional segments, a register or a memory can be set to store more information. For instance, as to the conditional segment with time period valued as "the latest" in FIGS. 5 to 7, a memory is set additionally for storing measurement time of patient data falling into the conditional segment. Each time when new data enters into this conditional segment, measurement time of the new data is compared to the stored measurement time. If the measurement time of the new data is later than the stored measurement time, then the measurement time of the new data replaces the formerly stored measurement time. If the measurement time of the new data is earlier than the stored measurement time, then the formerly stored measurement time is retained.

In an embodiment of the present invention, besides a plurality of conditional segments formed according to the method of FIG. 3, an "other" conditional segment is set additionally to contain data which does not belong to any one conditional segment formed according to the method. Alternatively, in another embodiment of the present invention, data which does not belong to any one conditional segment above is not recorded.

In another embodiment of the present invention, in order to avoid unnecessary data matching operations at step 82, step 80 (shown with dotted lines in FIG. 8) is executed before step 82, wherein the required patient data is determined based on the indication conditions so as to narrow down the range of patient data to be processed at step 82. Below, descriptions are made in connection with the examples of Indication Conditions 1-3, wherein the involved parameters include measurement item, reference standard, and time period.

In another embodiment of the present invention, the required patient data is obtained transversely based on values of specific parameters in the plurality of indication conditions. Specifically, step 80 can include determining the required patient data based on a union of value ranges of at least one parameter in the plurality of parameters defined in the indication conditions.

In another embodiment of the present invention, at step 80, the required patient data is determined based on a union of value ranges of the parameter "measurement item." Specifically, the measurement item is respectively valued as fasting blood glucose and 2 h blood glucose in Indication Conditions 1-3 and, thus, the union thereof is a collection of fasting blood glucose and 2 h blood glucose. Therefore, at step 80, data concerning the fasting blood glucose and 2 h blood glucose in the patient data is determined as the required patient data.

In another embodiment of the present invention, at step 80, the required patient data is determined based on a union of value ranges of the parameter "time period." Specifically, the time period is respectively valued as recent month, recent 3 months, and latest time in Indication Conditions 1-3 and, thus, the union thereof is the recent 3 months. Therefore, at step 80, all data in recent 3 months is determined as the required patient data.

In another embodiment of the present invention, two parameters are taken into consideration to determine the required patient data. In this case, step 80 can include, determining a first data portion based on a union of value ranges of a first parameter in the plurality of parameters defined in the indication conditions; determining a second data portion based on a union of value ranges of a second parameter in the plurality of parameters defined in the indication conditions; and determining an intersection of the first data portion and the second data portion as the required patient data.

In an example, measurement item is taken as the first parameter and time period is taken as the second parameter. According to analysis in the previous embodiments, data concerning the fasting blood glucose and 2 h blood glucose in the patient data can be determined as the first data portion and all data in recent 3 months can be determined as the second data portion. Then, data concerning the fasting blood glucose and 2 h blood glucose in recent 3 months can be determined as the required patient data by getting an intersection of the first data portion and the second data portion.

It can be appreciated, in case that more parameters are considered to determine the required patient data, based on the two data portions according to two parameters, another data portion can be determined according to a union of values of another parameter and then an intersection of the another data portion with the formerly obtained data portion is taken so as to further narrow down range of the patient data to be analyzed.

In another embodiment of the present invention, the required patient data can further be determined by considering respective indication conditions one by one. Specifically, step 80 can include determining data portions required by respective indication conditions based on definitions of respective indication conditions; and obtaining a union of data portions required by respective indication conditions as the required patient data.

In an example, the Indication Conditions 1-3 are taken into consideration one by one to determine the required data portions respectively. For instance, according to definition of the Indication Condition 1, it can be determined that the data portion required by the Indication Condition 1 includes data concerning the fasting blood glucose in one month and data concerning the 2 h blood glucose in one month of a patient. Similarly, the data portions required by the Indication Condition 2 and Indication Condition 3 are determined respectively. Then, a union of the data portions for respective indication conditions obtained is taken to determine the required patient data.

The processes of getting a union or intersection as to different value ranges and different data portions can be performed using various mathematical analysis methods in the prior art, which will not be explained further here.

Step 80 excludes data which cannot possibly fall into any conditional segment formed according to FIG. 3, reduces the amount of data to be analyzed at step 82, improves the processing efficiency of step 82, and, thus, facilitates the process of obtaining distribution information of the patient data in respective conditional segments.

Based on distribution information of the patient data in respective conditional segments, at step 84, a matching relation of the patient data with at least one indication condition of the plurality of indication conditions is analyzed based on the distribution information. For this purpose, a specific indication condition to be analyzed is firstly converted into operation as to data distribution of at least one conditional segment and then a matching relation of the patient data with the specific indication conditions is determined based on data distribution of the at least one conditional segment above.

For instance, Indication Condition 1 includes the following condition: 80% of blood glucose value in one month satisfies: fasting blood glucose<7.5 mmol/L. The condition can be converted into the following operation: obtaining a ratio of the number of measurement data concerning the fasting blood glucose in one month whose measurement result is <7.5 mmol/L to the total number of the data concerning the fasting blood glucose in one month and determining whether the ratio is lower than 80% or not. In the case that conditional segments for Indication Conditions 1-3 are formed as shown in FIG. 5B, the ratio above corresponds to the following expression: $(C(2)+C(4))/(C(2)+C(4)+C(6)+C(8))$, wherein $C(i)$ indicates data counting distributed in the conditional segment (i). Thus, the above ratio can be calculated directly by obtaining data distribution of conditional segments (2), (4), (6) and (8) (i.e. counting number of data falling therein) so as to determine whether the patient data matches the Indication Condition 1. The Indication Condition 2 can also be converted into similar operations. Indication Condition 3 can be converted into operation of judging whether counting of the conditional segment (1) is 0. As the conditional segments are formed based on respective indication conditions, the indication conditions can be easily converted into operations on data distribution results as to conditional segments. It can be appreciated, when matching analysis is performed as to respective indication conditions at step 84, it is only required to directly use the data distribution of respective conditional segments obtained in step 82 without needing to read, convert, or analyze the patient data again.

Therefore, in general, in the embodiments of the present invention described above, a plurality of conditional segments can be formed directed to a plurality of indication conditions. Then distribution information of the patient data in respective conditional segments can be obtained. Thus, for any indication condition, a matching relation of the patient data therewith can be directly determined based on the distribution information. Compared to the processing manner of performing data acquisition, conversion, and analysis as to each indication condition in the prior art, the embodiments of the present invention avoid chances of efficiency reduction caused by multiple data acquisitions, conversions, and analysis so as to realize more efficient processing and analysis of patient data.

Figure 9A:
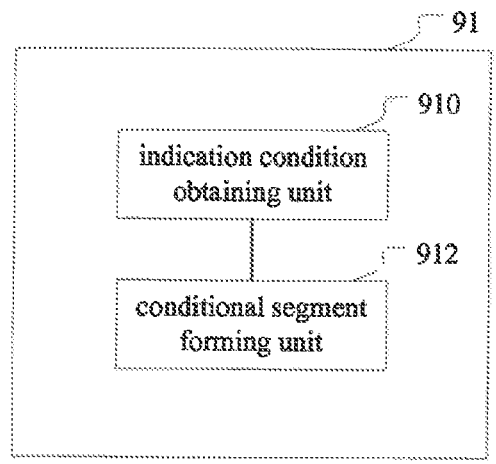
FIG. 9A shows a schematic block diagram of an apparatus for processing indication conditions according to an embodiment of the present invention.

Based on the same inventive concept, embodiments of the present invention further provide an apparatus for processing indication conditions and an apparatus for processing patient data. FIG. 9A shows a schematic block diagram of the apparatus for processing indication conditions according to an embodiment of the present invention. In FIG. 9A, the apparatus is indicated as a whole as 91. As shown in the Figure, the apparatus 91 for processing indication conditions includes: an indication condition obtaining unit 910 configured to obtain a plurality of predetermined indication conditions which relate to a plurality of parameters; and a conditional segment forming unit 912 configured to form a plurality of conditional segments based on respective values of the plurality of parameters defined in the plurality of indication conditions, wherein the plurality of conditional segments respectively correspond to a plurality of combinations of value ranges of the plurality of parameters.

According to an embodiment of the present invention, the conditional segment forming unit 912 includes (not shown): a first level forming module configured to select a first parameter from the plurality of parameters to form a first level of conditional segments based on values of the first parameter defined in the plurality of indication conditions; a range segment forming module configured to select another parameter from the rest of the parameters to form a plurality of range segments based on values of the another parameter defined in the plurality of indication conditions; and a combining module configured to combine the plurality of range segments with a higher level of conditional segments to form a new level of conditional segments; wherein the range segment forming module and the combining module are executed repeatedly until all the plurality of parameters are processed and the new level of conditional segments formed then is determined as the plurality of conditional segments.

According to an embodiment of the present invention, the combining module above is configured to combine the plurality of range segments with a higher level of conditional segments by taking association between a plurality of parameters defined in the plurality of indication conditions into consideration.

According to an embodiment of the present invention, the indication condition obtaining unit 910 is configured to obtain the plurality of indication conditions from a clinical guideline and the plurality of parameters, including measurement item, reference standard, and time period.

Figure 9B:
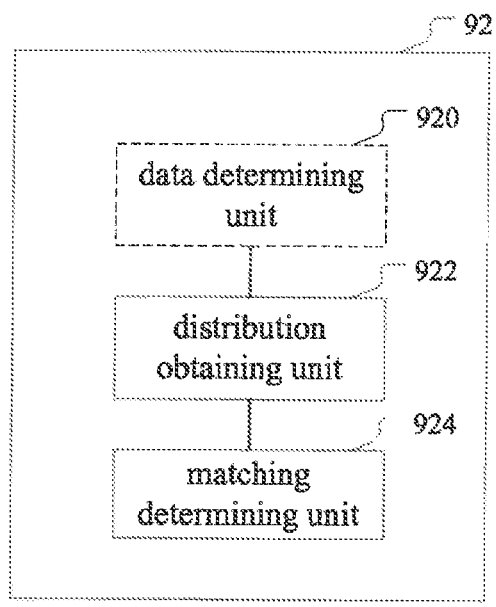
FIG. 9B shows a schematic block diagram of an apparatus for processing patient data according to an embodiment of the present invention.

FIG. 9B shows a schematic block diagram of an apparatus for processing patient data according to an embodiment of the present invention. In FIG. 9B, the apparatus is indicated as a whole as 92, including: a distribution obtaining unit 922 configured to obtain distribution information of the patient data in a plurality of conditional segments formed as to a plurality of indication conditions using the apparatus according to FIG. 9A; and a matching determining unit 924 configured to determine a matching relation of the patient data with at least one indication condition of the plurality of indication conditions based on the distribution information.

According to an embodiment of the present invention, the distribution obtaining unit 922 is configured to: count numbers of patient data falling into corresponding conditional segments using counters set for the plurality of conditional segments; and obtain distribution of the patient data in respective conditional segments by reading the counting of the counters of the plurality of conditional segments.

According to an embodiment of the present invention, the apparatus 92 further includes a data determining unit 920 (shown with dotted lines) configured to determine required patient data based on a union of value ranges of at least one parameter in the plurality of parameters defined in the plurality of indication conditions and the distribution obtaining unit is configured to determine distribution of the required patient data in the plurality of conditional segments.

According to an embodiment of the present invention, the data determining unit 920 is configured to determine a first data portion based on a union of value ranges of a first parameter in the plurality of parameters in the plurality of indication conditions; determine a second data portion based on a union of value ranges of a second parameter in the plurality of parameters in the plurality of indication conditions; and determine an intersection of the first data portion and the second data portion as the required patient data.

According to an embodiment of the present invention, the matching determining unit 924 is configured to: convert the at least one indication condition into an operation of data distribution of at least one condition segment; and determine a matching relation of the patient data with the at least one indication condition based on the data distribution of the at least one conditional segment.

Concrete executing manners of the apparatus 91 for processing indication conditions and apparatus 92 for processing patient data above can refer to the description of the method in connection with the concrete examples afore, which will not be detailed again.

The methods and apparatuses of the embodiments of the present invention reduce or avoid chances of efficiency reduction caused by multiple data acquisitions, conversions, and analysis so as to realize more efficient processing and analysis of patient data.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of code, which includes one or more executable instructions for implementing the specified logical function(s). It should also be noted that, in some alternative implementations, the functions noted in the block can occur out of the order noted in the figures. For example, two blocks shown in succession may, in fact, be executed substantially concurrently, or the blocks can sometimes be executed in the reverse order, depending upon the functionality involved. It is also noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, and/or to enable others of ordinary skill in the art to understand the embodiments disclosed herein.

What is claimed is:

1. A computer implemented method for processing a plurality of medical indication conditions on a computer that includes a processor communicatively coupled to a memory, the method comprising:
   obtaining a plurality of predetermined indication conditions which relate to a plurality of parameters;
   forming a plurality of conditional segments based on respective values of said plurality of parameters defined in said plurality of predetermined indication conditions,
      wherein each conditional segment of said plurality of conditional segments corresponds to a combination of different value ranges of respective parameters of said plurality of parameters, and
      wherein said plurality of predetermined indication conditions comprise a measurement item, a reference standard, a time period, a measurement condition, and a measurement manner; and
   obtaining a matching relation of the medical indication conditions with respective conditions of the predetermined indication conditions to analyze the medical indication conditions.

2. The computer implemented method according to claim 1, wherein the forming said plurality of conditional segments comprises:
   selecting a first parameter from said plurality of parameters to form a first level of conditional segments based on values of said first parameter defined in said plurality of indication conditions; and
   selecting an another parameter from the rest of said plurality of parameters to form a plurality of range segments based on values of said another parameter defined in said plurality of indication conditions.

3. The computer implemented method according to claim 2, wherein the combining said plurality of range segments with said higher level of conditional segments comprises:
   combining said plurality of range segments with said higher level of conditional segments by taking into consideration the association between said plurality of parameters defined in said plurality of indication conditions.

4. The computer implemented method according to claim 2, wherein the forming said plurality of conditional segments comprises:

dividing conditional segments of a higher level of the conditional segments to form a new level of conditional segments.

5. The computer implemented method according to claim 4, wherein the forming said plurality of range segments and the forming said new level of conditional segments are executed repeatedly until all said plurality of parameters are processed and said new level of conditional segments formed then is determined as said plurality of conditional segments.

6. The computer implemented method according to claim 1, wherein the forming said plurality of conditional segments comprises:
dividing conditional segments of a higher level of the conditional segments to form a new level of conditional segments.

7. A computer implemented method for processing a plurality of patient data, wherein the computer includes a processor communicatively coupled to a memory, the method comprising:
obtaining a plurality of predetermined indication conditions which relate to a plurality of parameters;
forming a plurality of conditional segments based on respective values of said plurality of parameters defined in said plurality of predetermined indication conditions, wherein each conditional segment of said plurality of conditional segments corresponds to a combination of different value ranges of respective parameters of said plurality of parameters,
obtaining a distribution information of said plurality of patient data in said plurality of conditional segments formed directed to said plurality of predetermined indication conditions; and
determining a matching relation of said plurality of patient data with an at least one indication condition of said plurality of predetermined indication conditions based on said distribution information,
wherein said plurality of predetermined indication conditions comprise a measurement item, a reference standard, a time period, a measurement condition, and a measurement manner.

8. The computer implemented method according to claim 7, wherein the obtaining said distribution information comprises:
counting the number of said plurality of patient data falling into a corresponding conditional segment using a plurality of counters set for said plurality of conditional segments; and
obtaining said distribution information of said plurality of patient data in said corresponding conditional segment by reading a counting of said plurality of counters set for said plurality of conditional segments.

9. The computer implemented method according to claim 7, further comprising:
determining a required patient data based on said plurality of indication conditions,
wherein the obtaining said distribution information comprises determining distribution of said required patient data in said plurality of conditional segments.

10. The computer implemented method according to claim 9, wherein the determining said required patient data comprises:
determining said required patient data based on a union of value ranges of an at least one parameter in said plurality of parameters defined in said plurality of indication conditions.

11. The computer implemented method according to claim 10, wherein the determining said required patient data further comprises:
determining a first data portion based on said union of value ranges of a first parameter in said plurality of parameters in said plurality of indication conditions;
determining a second data portion based on said union of value ranges of a second parameter in said plurality of parameters in said plurality of indication conditions; and
determining an intersection of said first data portion and said second data portion as said required patient data.

12. The computer implemented method according to claim 9, wherein the determining said required patient data comprises:
determining a plurality of data portions required by a respective indication condition based on a plurality of definitions of respective indication conditions; and
obtaining a union of said data portions required by said respective indication conditions as said required patient data.

13. The computer implemented method according to claim 7, wherein the determining said matching relation of said plurality of patient data with said at least one indication condition of said plurality of indication conditions based on said distribution information comprises:
converting said at least one indication condition into an operation of data distribution of an at least one condition segment; and
determining said matching relation of said plurality of patient data with said at least one indication condition based on said data distribution of said at least one conditional segment.

14. An apparatus for processing patient data, said apparatus comprising:
an indication condition obtaining unit configured to obtain a plurality of predetermined indication conditions which relate to a plurality of parameters;
a conditional segment forming unit configured to form a plurality of conditional segments based on respective values of said plurality of parameters defined in said plurality of predetermined indication conditions, wherein each conditional segment of said plurality of conditional segments corresponds to a combination of different value ranges of respective parameters of said plurality of parameters;
a distribution obtaining unit configured to obtain a distribution information of the patient data in said plurality of conditional segments formed directed to said plurality of predetermined indication conditions; and
a matching determining unit configured to determine a matching relation of said plurality of patient data with an at least one indication condition of said plurality of predetermined indication conditions based on said distribution information,
wherein said plurality of predetermined indication conditions comprise a measurement item, a reference standard, a time period, a measurement condition, and a measurement manner.

15. The apparatus according to claim 14, wherein said distribution obtaining unit is configured to:
count the numbers of said plurality of patient data falling into a corresponding conditional segment using a plurality of counters set for said plurality of conditional segments; and
obtain said distribution information of said plurality of patient data in said corresponding conditional segment by reading a counting of said plurality of counters set for said plurality of conditional segments.

16. The apparatus according to claim 14, further comprising a data determining unit configured to:
   determine a required patient data based on said plurality of indication conditions,
   wherein the distribution obtaining unit is configured to determine distribution of said required patient data in said plurality of conditional segments.

17. The apparatus according to claim 16, wherein the data determining unit is configured to determine said required patient data based on a union of value ranges of an at least one parameter in said plurality of parameters defined in said plurality of indication conditions.

18. The apparatus according to claim 17, wherein said data determining unit is configured to:
   determine a first data portion based on said union of value ranges of a first parameter in said plurality of parameters in said plurality of indication conditions;
   determine a second data portion based on said union of value ranges of a second parameter in said plurality of parameters in said plurality of indication conditions; and
   determine an intersection of said first data portion and said second data portion as said required patient data.

19. The apparatus according to claim 16, wherein said data determining unit is configured to:
   determine a plurality of data portions required by a respective indication conditions based on a plurality of definitions of respective indication conditions; and
   obtain a union of said data portions required by said respective indication conditions as said required patient data.

20. The apparatus according to claim 14, wherein said matching determining unit is configured to:
   convert said at least one indication condition into an operation of data distribution of an at least one condition segment; and
   determine said matching relation of said plurality of patient data with said at least one indication condition based on said data distribution of said at least one conditional segment.

* * * * *